US006723561B2

(12) United States Patent
Russell et al.

(10) Patent No.: US 6,723,561 B2
(45) Date of Patent: Apr. 20, 2004

(54) MATERIALS AND METHODS RELATING TO THE TRANSFER OF NUCLEIC ACID INTO QUIESCENT CELLS (75) Inventors: Stephen James Russell, Cambridge (GB); Adele Kay Fielding, Cambridge (GB); Colin Maurice Casimir, London (GB)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/043,665

(22) PCT Filed: Sep. 30, 1996

(86) PCT No.: PCT/GB96/02405

§ 371 (c)(1),
(2), (4) Date: Oct. 5, 1998

(87) PCT Pub. No.: WO97/12049

PCT Pub. Date: Apr. 3, 1997

(65) Prior Publication Data

US 2003/0007952 A1 Jan. 9, 2003

(30) Foreign Application Priority Data

Sep. 28, 1995 (GB) .............................. 9519776

(51) Int. Cl.[7] .......................... C12N 5/00; C12N 15/09; C11N 15/63
(52) U.S. Cl. .................... 435/377; 435/375; 435/320.1; 435/325; 435/455; 435/372
(58) Field of Search .............................. 435/320.1, 325, 435/366, 372, 373, 377, 375, 455; 424/93.1, 93.2, 93.21

(56) References Cited

U.S. PATENT DOCUMENTS

| 5,447,851 A | * | 4/1995 | Beutler et al. | ............. 435/69.7 |
| 5,554,512 A | * | 9/1996 | Lyman et al. | ............... 435/69.5 |
| 5,736,387 A | * | 4/1998 | Paul et al. | ............... 435/320.1 |

FOREIGN PATENT DOCUMENTS

| WO | WO 93/00103 | 1/1993 |
| WO | WO 93/25234 | 12/1993 |
| WO | WO 94/06920 | 3/1994 |
| WO | WO 94/27643 | 12/1994 |
| WO | WO 96/00294 | 1/1996 |
| WO | WO 96/33281 | 10/1996 |

OTHER PUBLICATIONS

D Lambrigts et al., Transplantation, "Discordant Organ Xenotransplantation in Primates," Sep. 1998, vol. 66, No. 5, pp. 547–561.*
M Maurice et al., Blood, "Efficient Gene Delivery to Quiescent Interleukin–2 (IL–2)–Dependent Cells by Murine Leukemia Virus–Derived Vectors Harboring IL–2 Chimeric Envelopes Glycoproteins," Jul. 1999, vol. 94, No. 2, pp. 401–410.*
PD Phillips et al., Journal of Cellular Physiology, "Renewed DNA Synthesis in Senescent WI–38 Cells by Expression of an Inducible Chimeric c–fos Construct," (1992), 151: 206–212.*
DB Luskey et al., Blood, "Stem Cell Factor, Interleukin–3, and Interleukin–6 Promote Retroviral–Mediated Gene Transfer Into Murine Hematopoietic Stem Cells," Jul. 1992, vol. 80, No. 2, pp. 396–402.*
Kohn DB. Clin. Exp. Immunol. 107:54–57, 1997.*
Briones et al. Haematologica 84:483–488, 1999 (abstract only).*
Anderson WF Nature 392:25–30, 1998.*

* cited by examiner

Primary Examiner—Ram R. Shukla
(74) Attorney, Agent, or Firm—Fish & Richardson P.C., P.A.

(57) ABSTRACT

Materials and methods for transferring nucleic acid encoding a polypeptide for treating a disease or disorder into populations of quiescent cells such as haematopoietic stem cells (HSCs), using retroviral packaging cell lines and retroviral particles expressing and display a growth factor such as stem cell factor (SCF) on the cell surface or as a fusion with a viral envelope protein. The present invention also relates to compositions comprising the retroviral packaging cell lines and retroviral particles, and their use in methods of medical treatment, in vivo and ex vivo.

8 Claims, 9 Drawing Sheets

A: TF-1 CELLS INCUBATED WITH 25 ng/ml rhSCF
B: TF-1 CELLS INCUBATED WITH AM12 CELLS EXPRESSING CELL SURFACE SCF (I.E. THE lacJP CELLS)
C: TF-1 CELLS INCUBATED WITH AM12 CELLS ONLY

MATERIALS AND METHODS RELATING TO THE TRANSFER OF NUCLEIC ACID INTO QUIESCENT CELLS

This is application is the U.S. national stage application of International application Serial No. PCT/GB96/02405, filed Sep. 30, 1996, which claimed priority from Great Britain patent application Serial No. 9519776.0, filed Sep. 28, 1995, and claims the benefit of the filing dates thereof under 35 U.S.C. §119.

FIELD OF THE INVENTION

The present invention relates to materials and methods for transferring nucleic acid encoding a polypeptide for treating a disease or disorder into populations of quiescent cells such as haematopoietic stem cells (HSCs), using retroviral packaging cell lines and retroviral particles expressing and displaying a growth factor such as stem cell factor (SCF) on the cell surface or as a fusion with a viral envelope protein. The present invention also relates compositions comprising the retroviral packaging cell lines and retroviral particles, and their use in methods of medical treatment, in vivo and ex vivo.

BACKGROUND TO THE INVENTION

The development of somatic gene therapy as a treatment for single gene inherited diseases and some acquired conditions, such as certain types of cancer, represents one of the most important technical advances in medicine. Blood related disorders such as the X-linked immunodeficiencies, or chronic granulomatous disease (CGD), are amongst the most favourable candidates as model systems for the evolution of this technology. The general feasibility of gene therapy for disorders of this type has been amply demonstrated by the results obtained in the treatment adenosine deaminase dependent severe combined immunodeficiency (ADA-SCID) using peripheral blood T-cells.

However, many problems stand in the way of the realisation of the promise of these techniques. For example, in the experiments described above, the T-cells including the genes required by the patients are not immortal, requiring the therapy to be repeated at regular intervals. Further, attempts to effect a permanent correction, for example by gene transfer into pluripotent haematopoietic stem cells (PHSC), have thus far been unsuccessful.

There are a number reasons for this. Firstly, PHSC are very rare in the bone marrow cell population, and so although work has been done on bone marrow cell culture, it is very difficult to draw conclusions from this work regarding PHSCs. Further, in humans there is a dearth of markers to identify PHSC and, at present, the most reliable marker of immature human bone marrow cells is the CD34 antigen, which marks about 1–2% of total marrow cells. However, probably only about 0.1% of these CD34+ cells are true PHSC. In addition, there are no wholly reliable assays for human PHSC, unlike murine systems, where the rescue of lethally irradiated individuals can be used to test for PHSC.

Recently, a method to enrich for PHSC has been described by Beradi et al (Science, 267, 104–108, (1995)) which exploits the quiescence of PHSCs as a basis for their functional isolation. In this method, bone marrow cells were incubated for 7 days in the presence of the cytokines stem cell factor (SCF) and IL-3, to stimulate division in all of the progenitor cells, but not in true PHSC. The cytotoxic agent, 5-fluorouracil (5-FU), was then added to these cultures, resulting in the death of all dividing cells in the culture. However, quiescent cells, including PHSC which average only 1 in $10^5$ of the original cells, were spared in this process. Accordingly, the authors reported obtaining an enriched population of cells having the characteristics of true PHSC.

However, the authors of this paper were unable to find any combination of cytokines that was able to stimulate these cells to divide, other than incubation in long term marrow culture (LTC), which also leads to their differentiation.

Thus, although, this method produces highly enriched populations of PHSC, it is their quiescence, the very property exploited for their isolation by Beradi et al, that still represents the most significant hurdle limiting current gene therapy protocols. This is because most highly developed vector systems presently used for gene transduction are based on murine retroviruses and these viruses (and the vectors derived from them) are unable to stably integrate their genome into non-dividing cells, rendering PHSCs refractory to retroviral gene transfer.

Previously, we presented an abstract at the European Working Group for Gene Therapy in November 1994 disclosing that a retroviral cell line containing a viral vector incorporating nucleic acid encoding GCD and expressing stem cell factor on its surface was able to achieve improved rates of transduction in a bone marrow cell culture. However, as mentioned above this cell culture contains a very low proportion of PHSC, and this treatment would not be expected to stimulate the PHSC to divide or to allow the stable integration of the nucleic acid encoding GCD into the PHSC genome. An important fact underlying this expectation is that in Beradi et al, stem cell factor was one of the cytokines used to stimulate selectively division in the most of the cells in marrow cell culture (but not the PHSC), allowing them to be killed to leave the enriched population of stem cells.

SUMMARY OF THE INVENTION

The present invention is based on the unexpected finding that it is possible to get haematopoeitic stem cells to cycle transiently during the period of exposure to vectors incorporating nucleic acid encoding a desired protein or polypeptide by exposing them to bound growth factors such as stem cell factor. This observation means that contrary to prior expectations, a population of quiescent cells such as PHSC can be used as targets for vectors incorporating nucleic acid encoding a desired protein or polypeptide, provided that the cells are additionally exposed to a surface bound growth factor, e.g. stem cell factor expressed by a retroviral packaging cell line so that it is bound on the cell surface or expressed as a fusion with an envelope protein of retrovirus so that the growth factor is displayed on the surface of the retrovirus.

Without wishing to be bound by any particular theory, we believe that the exposure of the quiescent cells to the membrane or surface bound growth factor induces them to start dividing, so that the nucleic acid, e.g. packaged in retroviral particles produced by a retroviral packaging cell line, can infect the cells and become incorporated into their genomes which become accessible during cellular division when the nuclear membrane dissolves. This method has the advantage that it can be adapted for the treatment of a wide variety of disorders, by incorporating nucleic acid encoding an appropriate protein or polypeptide into the vector. A further advantage of the method is that by stimulating the quiescent cells to differentiate at the time of gene transfer, preferential amplification of the transduced cells relative to the non-transduced cells can be achieved.

Accordingly, in a first aspect, the present invention provides a retroviral packaging cell line transformed with a viral vector comprising nucleic acid encoding a polypeptide for treating a disease or disorder, the retroviral packaging cell line being capable of expressing nucleic acid encoding a growth factor so that the growth factor is (i) displayed on the cell surface or (ii) expressed as a fusion with a viral envelope protein so that the growth factor is displayed on the surface of viral particles, wherein the cell line packages the nucleic acid encoding the polypeptide in viral particles produced by the retroviral packaging cell line, the cell line being for use in a method of medical treatment of a disease or disorder that responds to the polypeptide.

In this aspect, the retroviral packaging cell line includes nucleic acid encoding viral envelope protein so that the cell line can produce viral particles and package the nucleic acid encoding the polypeptide for treating the disease or disorder in them.

In this application, "quiescent" refers to cells that are unlikely to enter mitosis within the next 24 hours in the absence of appropriate growth stimulus. Preferably, the population of quiescent cells are enriched in haematopoeitic stem cells, for instance by employing the isolation method of Beradi et al (supra) using bone marrow cells. Other quiescent cell types suitable for use in the invention include resting T-lymphocytes, B-lymphocytes and monocytes, stem cells of non-haematopoietic tissues such as liver and muscle, epithelial stem cells in skin, gut, bladder and airways, vascular endothelial cells, quiescent neoplastic cells and germ cells such as sperm progenitors.

In a further aspect, the present invention provides retroviral particles displaying surface bound growth factor as a fusion with an envelope protein, the particles being produced by the retroviral packaging cell line as set out above.

In one embodiment, the surface bound growth factor is provided by engineering the retroviral packaging cell line to express growth factor on its surface by transfecting the cell line with nucleic acid encoding the growth factor.

In an alternative embodiment, a retroviral vector expressing surface bound growth factor (e.g. SCF) could be prepared by constructing a packaging cell line engineered to produce a chimeric retroviral envelope protein fused to all or part of the growth factor. The growth factor can be used to replace the natural binding domain of the envelope protein, or can be fused directly to the C- or N- terminus of a retroviral envelope protein. Such chimeric envelopes have been described for use in retroviral targeting (7–9). In this embodiment, the retroviral packaging cell line may also display the growth factor-envelope protein fusion on the surface of the retroviral packaging cell line. The chimeric envelope could be expressed as the sole viral envelope protein in an attempt to target the retrovirus to stem cells, as well as to transduce a growth signal, or in concert with the "wild type" envelope protein, to induce growth in growth factor responsive target cells, without targeting to a specific cell type. The former strategy is more applicable to an in vivo situation, the latter to an in vitro transduction process. An example of this is the expression of the growth factor as a fusion with viral envelope SU protein of murine leukemia virus (MLV).

In some instances, expressing the growth factor as a fusion with a viral envelope protein, may lead to the nucleic acid encoding the polypeptide not being incorporated into the genome of the target quiescent cells. This can be overcome by introducing a cleavable linker between the viral envelope protein and the growth factor so that the growth factor can be cleaved from the viral particle by addition of a cleaving agent, typically once the quiescent cells start dividing. An example of such a system is the use of a chimeric envelope protein in which viral envelope protein is linked to a factor $X_a$ linker which is in turn linked to the growth factor. In this system, factor $X_a$ protease can be used to cleave the growth factor from the surface of the viral particles, so that the particles can transfer the nucleic acid encoding the polypeptide to the target cells where it can be incorporated into their genomes.

Preferably, the surface bound growth factor is FLT3-ligand, or stem cell factor, also known as mast cell growth factor, kit ligand factor or Steel factor. Nucleic acid sequences encoding stem cell factors are described in WO92/00376, e.g. the Δ28 MGF stem cell factor.

Preferably, the vector is a retroviral vector such as MFG or the pBabe vector series. Alternatively, present invention could employ a lentiviral vector producer cell line. In the viral display aspect of the invention, as it is known that the envelope glycoproteins of lentiviral vectors can be substituted by the envelope proteins of C-type retroviruses, the chimeric envelope glycoproteins described below could be used with lentiviral vectors such as those based on HIV, CAEV or Visna. Further vectors suitable for use in the methods described herein can be readily identified by the skilled person.

Typically, the desired protein or polypeptide will be one that a patient is unable to synthesise in his or her body or does not synthesise in the usual amount. An example of this is the use of gene therapy to treat adenosine deaminase dependent severe combined immunodeficiency (ADA-SCID). However, the concepts described herein are applicable to situations in which the nucleic acid encodes a protein or polypeptide that binds a substance that is overexpressed in a patient's body, e.g. causing some harmful physiological effect, or a protein or polypeptide that can bind to a polypeptide that is produced in a patient's body in an inactive form to activate it or in an active form to inactivate it. Preferably, the use of the present invention in these applications has the advantage that the therapy provided by transfecting the stem cells is long lasting or permanent, thereby helping to avoid the need for frequently repeated treatment.

Diseases that might be treated using the methods and materials described herein include all forms of chronic granulomatous disease (CGD), all forms of severe combined immunodeficiency (SCID), hyper gamma globulinaemia syndrome (hyper IgM), Wiskott-Aldrich Disease (WAS), thallassaemia, sickle-cell anaemia, other anaemias due to deficiencies of red blood cell proteins, neutrophil defects due to failure to synthesise granule components, e.g. myeloperoxidase deficiency, haemophilia and other clotting disorders such as complement deficiencies, lysomal storage disorders, such as Gaucher's disease, Hurler's disease, and mucopolysaccharidosis, leukocyte adhesion deficiency (LAD), bare lymphocyte syndrome, cancer and AIDS.

Other applications of the invention include the genetic modification of haematopoietic stem cells to repopulate the immune system with genetically modified T-lymphocytes that resist HIV, the genetic modification of haematopoeitic stem cells to repopulate bone marrow with haematopoietic progenitors that resist the myelosuppressive effects of cytotoxic chemotherapy, and the genetic modification of T-lymphocytes with chimeric T-cell receptors to target cytotoxic T-cells against tumours or virally infected cells.

In a further aspect, the present invention provides compositions comprising a retroviral packaging cell line or retroviral particles set out above, in combination with a suitable carrier. In this aspect, the present invention provides pharmaceutical compositions suitable for delivering nucleic acid encoding a desired polypeptide to a population of stem cells in vitro, e.g. to prepare engineered stem cells for subsequent implant into a patient. Alternatively, the composition could be used in vivo, to directly deliver the nucleic acid to a patient's own stem cells. In this case, the composition preferably comprises a retroviral vector incorporating the nucleic acid encoding a desired protein or polypeptide and displaying a growth factor on its surface, e.g. as part of an envelope protein.

In a further aspect, the present invention provides the use of a retroviral cell line or retroviral particles as described above in the preparation of a medicament for treating a disease or disorder that responds to the polypeptide encoded by the nucleic acid packaged in the retroviral particles.

In this aspect, preferably the medicament comprising the retroviral packaging cell line or retroviral particles is administered by implantation into a patient's bone marrow or is administered by infusion into a patient's blood. In order to allow the packaging cells to target the bone marrow when administered by infusion, advantageously, receptors such as integrins can be expressed on the surface of the cells. Alternatively or additionally, the immunogenicity of the packaging cells can be reduced by expressing an immunosuppressive factor such as FAS-ligand on the cell surface which can bind to activated T-cell FAS-receptors, triggering the T-cells to die by apoptosis. FAS-ligand expressing allogeneic cell implants have previously been shown to resist immune mediated rejection.

In a further aspect, the present invention provides a method of transforming a population of quiescent cells with nucleic acid encoding a polypeptide so that the nucleic acid is incorporated into the genome of the cells, the method comprising exposing the cells to a retroviral packaging cell line or retroviral particles as described above, wherein the surface bound growth factor induces the cells to divide, so that the nucleic acid encoding the polypeptide for treating a disease or disorder contained in the viral particles can incorporate into the genome of the cells.

In this aspect, preferably the quiescent cells are a population of bone marrow cells enriched in haematopoeitic stem cells.

In further aspects, the present invention provides a population of cells produced by the above method having the nucleic acid encoding a polypeptide for treating a disease or disorder stably incorporated into their genome, and pharmaceutical compositions comprising these populations of cells.

In a further aspect, the present invention provides a method for introducing nucleic acid encoding a polypeptide for treating a disease or disorder into the genome of a population of cells in viva, the method comprising administering a retroviral packaging cell line or retroviral particles by implantation into a patient's bone marrow or by infusion into a patient's blood.

By way of example, the present invention will now be described in more detail with reference to the accompanying figures. The following examples are provided to illustrate the present invention, and should not be interpreted as limiting the scope of the claims.

BRIEF DESCRIPTION OF THE FIGURES

FIG. 2. Tritiated thymidine labelling of 5-FU selected cells. Bone marrow cells were incubated as described earlier for 7 days in 5-FU [A], or not [B], after which tritiated ($^3$H) Thymidine was added to the medium and the cells incubated for a further 16 hrs. Following this incubation they were pelleted onto glass microscope slides using Cytospin (Shandon Instruments). The slides were dipped in photographic emulsion (Ilford) and allowed to dry before incubation in the dark at −70° C. for one week. The slides were then developed using standard developer and fixer and counter stained with Wright's stain. Cells undergoing division are labelled by the incorporation of $^3$H thymidine into DNA, which leads to the formation of silver grains in the emulsion. The 5-FU treated cells (panel A) show no labelling indicating quiescence, whereas the untreated cells (panel B) show extensive and intense labelling indicative of active cell division.

DETAILED DESCRIPTION

Materials and Methods

Cell Culture

Bone marrow cells were harvested and stem cells selected using the 5FU technique transduced with retroviral vectors and incubated in long term bone marrow culture all as described in the original application. TF-1 cells were maintained in RPMI medium supplemented with 10% fetal calf serum, 2 mM glutamine, penicillin and streptomycin. Recombinant human GM-CSF was added to 200 pg/ml for routine passage and recombinant human SCF at 25 ng/ml was used for short term growth support. Packaging and producer cell lines were cultured under the conditions described below and irradiated (500 rads) prior to use in culture experiments.

PCNA Staining

Staining of cells for proliferating cell nuclear antigen (PCNA) was performed on cells spun onto microscope slides using a Cytospin (Shandon Instruments) and fixed in methanol, using a mouse anti-human monoclonal antibody (Dako) directly conjugated to FITC. Cells were incubated for 1 hour at room temperature before the antibody solution was washed away with PBS, the slides air-dried, cover-slipped using Citifluor and the fluorescence viewed under UV light using a Zeiss microscope.

Construction of LacZ Retroviral Producer Cells Expressing Surface SCF

A retroviral producer line established in the packaging line AM12 and containing the retroviral vector genome nlsLacZ (12) was used as a target to introduce the plasmid pJP2 by calcium phosphate transfection as described in the original submission. Cells were selected for the presence of the SCF-encoding plasmid using the linked histinidol resistance marker, as described previously.

Proliferation Assays

Cells were washed twice in PBS pelleted and resuspended in media without growth factor and incubated overnight. Cytokines and $^3$H thymidine (10 $\mu$Ci) were added to the media and the cells incubated for a further 24 hours. The cells were then harvested using a Titertek cell harvester and the incorporated radioactivity counted using a scintillation counter.

X-gal Staining

For assessing retroviral gene transfer, TF-1 cells were deposited onto microscope slides using a Cytospin (Shandon Instruments) and fixed in PBS buffer containing 0.5% glutaraldehyde. β-galactosidase activity was detected by staining the cells in situ with 0.1% X-gal (5chloro-4bromo-3indolyl-β-D-galactopyranoside.) in PBS buffer containing, 0.01% sodium deoxycholate, 0.02% NP40, 2 mM MgCl$_2$, 5 mM potassium ferricyanide and 5 mM potassium ferrocyanide for 1–2 hours at 37° C.

Tritrated Thymidine Labelling

For $^3$H thymidine labelling TF-1 cells were transduced with retroviral vector as described above in RPMI media to which 10 $\mu$Ci of $^3$H thymidine was added. After overnight labelling, the cells were deposited onto microscope slides and stained for β-galactosidase activity before being washed dried and dipped in photographic emulsion. The emulsion was allowed to air dry overnight and the slides were exposed at –70° C. in a light tight box for 3 days. To visualise the $^3$H thymidine incorporation the emulsion was developed and fixed using standard X-ray film developer and fixer and cells producing silver grains were assessed by light and dark field light microscopy.

EXAMPLE 1

Retroviral Transduction of Quiescent Target Cells with Retroviral Producer Cells Expressing Surface Growth Factor (SCF); the Establishment of a Model System To demonstrate the feasibility of using producer cells that express surface growth factor to transduce quiescent cells with retroviral vectors, we have developed a model system using the growth factor-dependent cell line TF-1 (12) . This cell line was developed from an erythroleukaemic patient and probably equates to cell arrested at an early stage of megakaryocyte development. The cells can only be grown in the presence of growth factors, the most usual being IL-3 or GM-CSF to which they respond very sensitively. They also are capable of dividing in response to SCF though this response is significantly weaker. These cells can easily be rendered quiescent by withdrawal of growth factor support. We used these cells as targets for retroviral transduction, following induction of quiescence.

Figure 3:
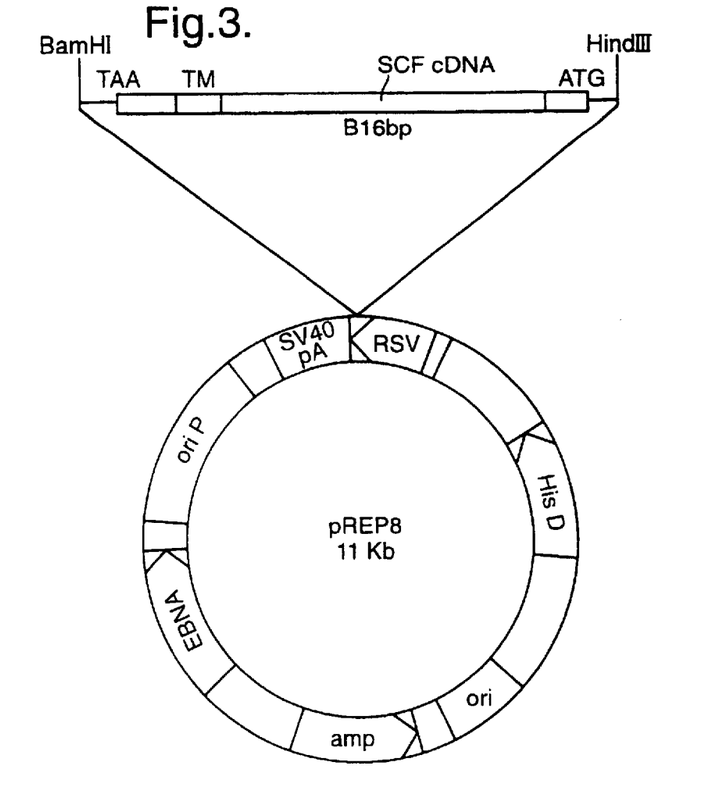
FIG. 3 shows the restriction map of plasmid pJP2 carrying SCF cDNA.
Figure 4:
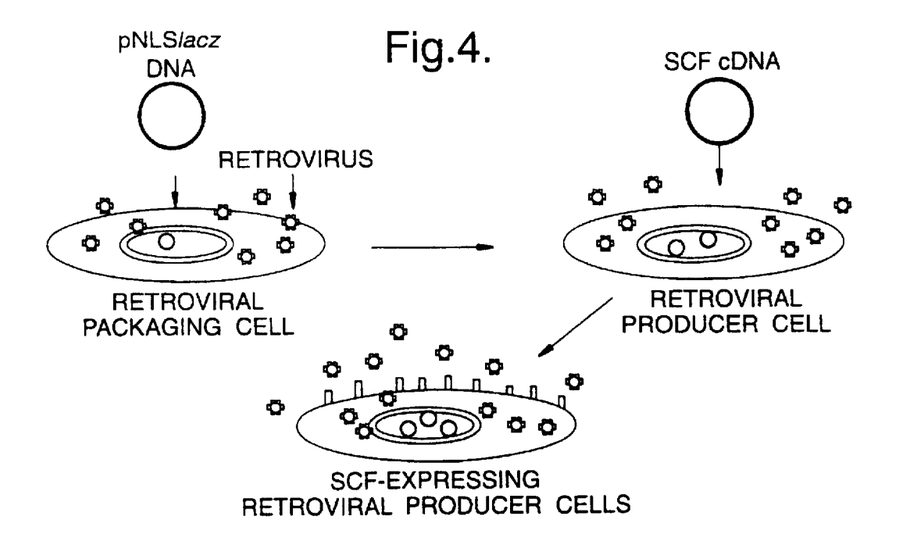
FIG. 4 shows schematically the construction of retroviral packaging cell lines expressing membrane-bound SCF.

In order to facilitate this analysis, we constructed a retroviral producer line expressing surface SCF (see FIG. 4). This was done by transfecting the same plasmid we had constructed before containing the hSCF cDNA (plasmid pJP2, FIG. 3), into retroviral producer cells transducing a retroviral vector encoding the gene for β-galactosidase (NLSlacZ). This bacterial enzyme can be used in conjunction with synthetic substrates to produce a blue staining reaction when active enzyme is present. Accordingly, in these experiments, successfully transduced cells will stain blue following retrovirally mediated gene transfer. The resulting producer line was identified as LacJP. Immunofluorescent staining of the LacJP cell line with anti-SCF antibody showed the presence of the surface bound SCF.

Figure 5:
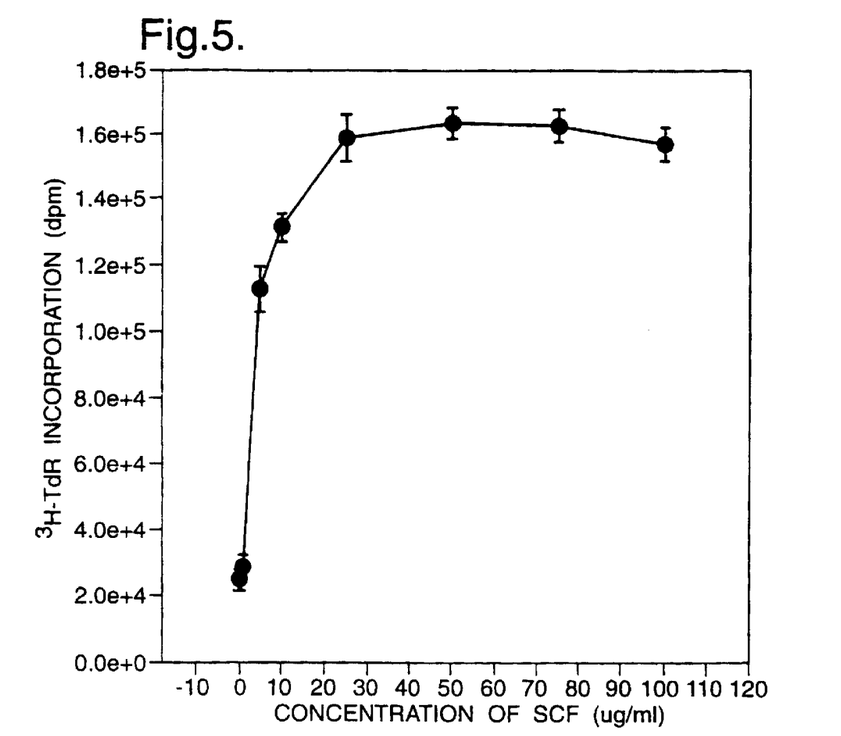
FIG. 5 shows the proliferative response of TF-1 cells to soluble SCF and the membrane bound growth factor. To start this analysis we titrated soluble SCF to against TF-1 cells to establish the optimum concentration of SCF
Figure 6:
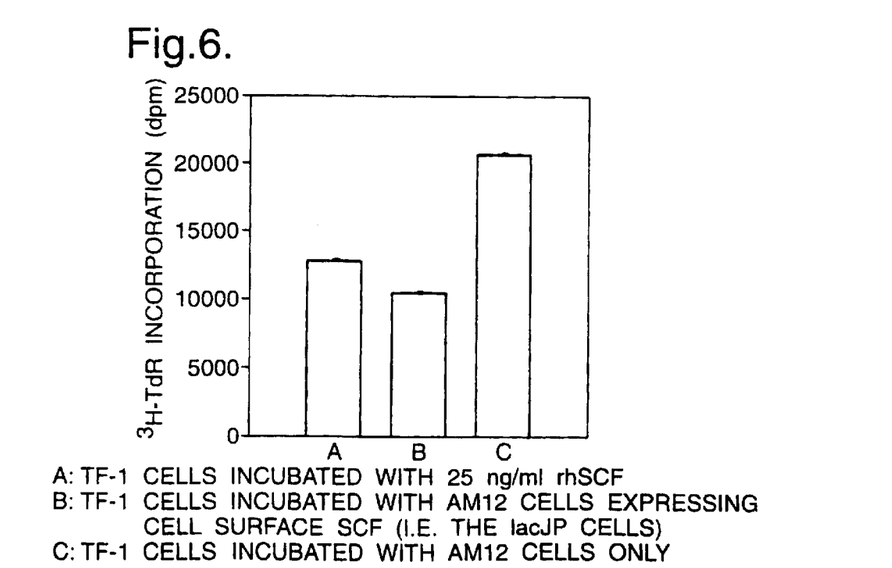
FIG. 6 shows the results of a proliferation assay on TF-1 cells demonstrating that TF-1 cells have a proliferative response to the AM12 cell line alone due to the production of IL6 by the cell line.
Figure 7:
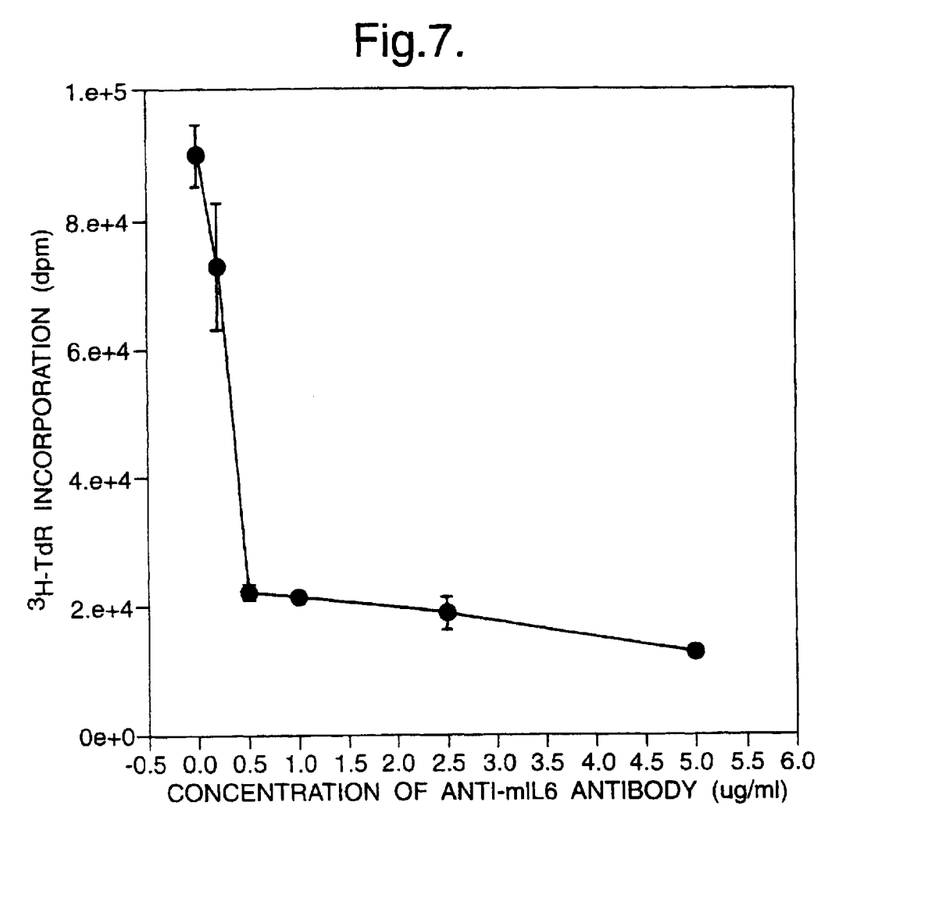
FIG. 7 shows the titration of anti-IL6 antibody and its effect on the proliferative response of TF-1 cells incubated with AM12 cells only, demonstrating that it is possible to test for SCF-mediated transduction of quiescent TF-1 cells co-cultured with retroviral producer cells by blocking the IL6-dependent proliferation using anti-IL6 antibody.

We compared the proliferative response of TF-1 cells to soluble SCF and the membrane bound growth factor. To start this analysis we titrated soluble SCF to against TF-1 cells to establish the optimum concentration of SCF (FIG. 5). TF-1 cells were then grown in the presence of soluble recombinant human SCF or in the presence of the lac JP cell line or the parent packaging cell line (AM12). These initial experiments quickly revealed, however, that the retroviral packaging cell line produced a growth factor that was a potent mitogen for the TF-1 target cells (FIG. 6) . It was previously described in the literature that packaging cells lines were sources of the cytokine IL-6. We hypothesised that mitogen secreted by the retroviral packaging cells might be IL-6. To test this we attempted to block the response to IL-6 in our cultures by the addition of neutralising antibody to the cytokine. Titration of the neutralising antibody (FIG. 7) demonstrated that it was possible to completely eradicate the IL-6 mediated proliferative response of TF-1 cells when co-cultured with retroviral producer cells. All the subsequent experiments were therefore performed in the presence of inhibitory amounts of anti-IL-6.

We then tested the ability of our modified producer cells to facilitate transduction of quiescent target cells. TF-1 cells in exponential growth were removed from growth factor and incubated overnight to allow them to become quiescent. TF-1 cells were then co-cultured overnight with the retroviral producer cells expressing surface SCF or the parent producer line. Following co-culture, the TF-1 cells were removed collected onto microscope slides and stained for β-galactosidase production. Cells that were co-cultured on the parent producer line showed no evidence for retroviral transduction. In contrast, approximately 3% of cells that were co-cultured with the SCF producer cells were found to be positively staining. These were confirmed as cycling TF-1 cells by doubly-labelling the cells with titrated thymidine ($^3$H). This radioactive nucleoside becomes incorporated into the DNA of dividing cells and can be detected by autoradiographic deposition of silver grains in a photographic emulsion into which the slides have been dipped. As expected, many of the transduced TF-1 cells also showed the presence of silver grains indicating that cell division had taken place.

Thus, these experiments show that expression of a surface bound growth factor by retroviral producer cell lines is able to facilitate the retroviral transduction of a quiescent target cell population and therefore enable the retroviral-mediated transfer of genes to cells that would normally be refractory to this technique.

EXAMPLE 2

Retroviral Transduction using Populations of Cells Isolated from Umbilical Cord Blood We carried out a transduction experiment similar to those described above using haematopoietic progenitor cells obtained from human umbilical cord blood. Progenitors were selected from cord blood using the Macs™ (Miltenyi Biotech) system to isolate CD34+ progenitor cells (15). The CD34+ population in cord blood is made up extensively of quiescent cells (13, 16). These cells were transduced in vitro as described above by co-culture for 48 hours in the presence of the nlsLacz producers or the LacJP producers. The cord blood cells were then harvested and pelleted onto microscope slides and stained for β-galactosidase activity as described above. Cells that had been exposed to the nlsLacZ producers had a low proportion of blue-staining cells (<10%), whereas those that had been exposed to the LacJP producers that expresses SCF on its surface had a very high proportion of blue-stained cells (>80%). In addition, blue-staining colonies formed by subsequent growth of these populations of cells in semisolid media were only found in cultures derived from cells that had been co-cultured with the LacJP cell line.

EXAMPLE 3

Retroviral Transduction of Haematopoietic Stem Cells using a Retroviral Packaging Cell Line Expressing Surface Bound SCF (a) Production of the Retroviral Packaging Cell Line The cell line 1MI-ΔSCF was constructed as follows: the parent producer cell line 1MI was derived from the Am12 packaging cell line (1), by calcium phosphate-mediated DNA transfection, using the retroviral vector encoding the p47-phox cDNA we described previously (2), with the exception that the neomycin resistance cassette was removed. The retroviral backbone is derived from the pBabe series of vectors described by Morgenstern et al (3). High titre producer clones were then selected by "dot blot" analysis of successful transfectants. The 1MI producer line was then transfected as described above using the plasmid pJP2 (FIG. 3) encoding the membrane-associated form of the human stem cell factor (SCF). Cells expressing SCF were selected using histidinol. Individual clones were grown out and tested for expression of SCF by immunofluorescence with a labelled anti-SCF antibody. The plasmid pJP2 was constructed by insertion of an 816 bp HindIII to BamHl, SCF cDNA fragment into the mammalian cell expression plasmid pREP8 (Invitrogen Corp). The SCF cDNA was excised from the plasmid BSSK: huMGFΔ28, see WO92/00376.

(b) Selection and Transduction of PHSC

Figure 1:
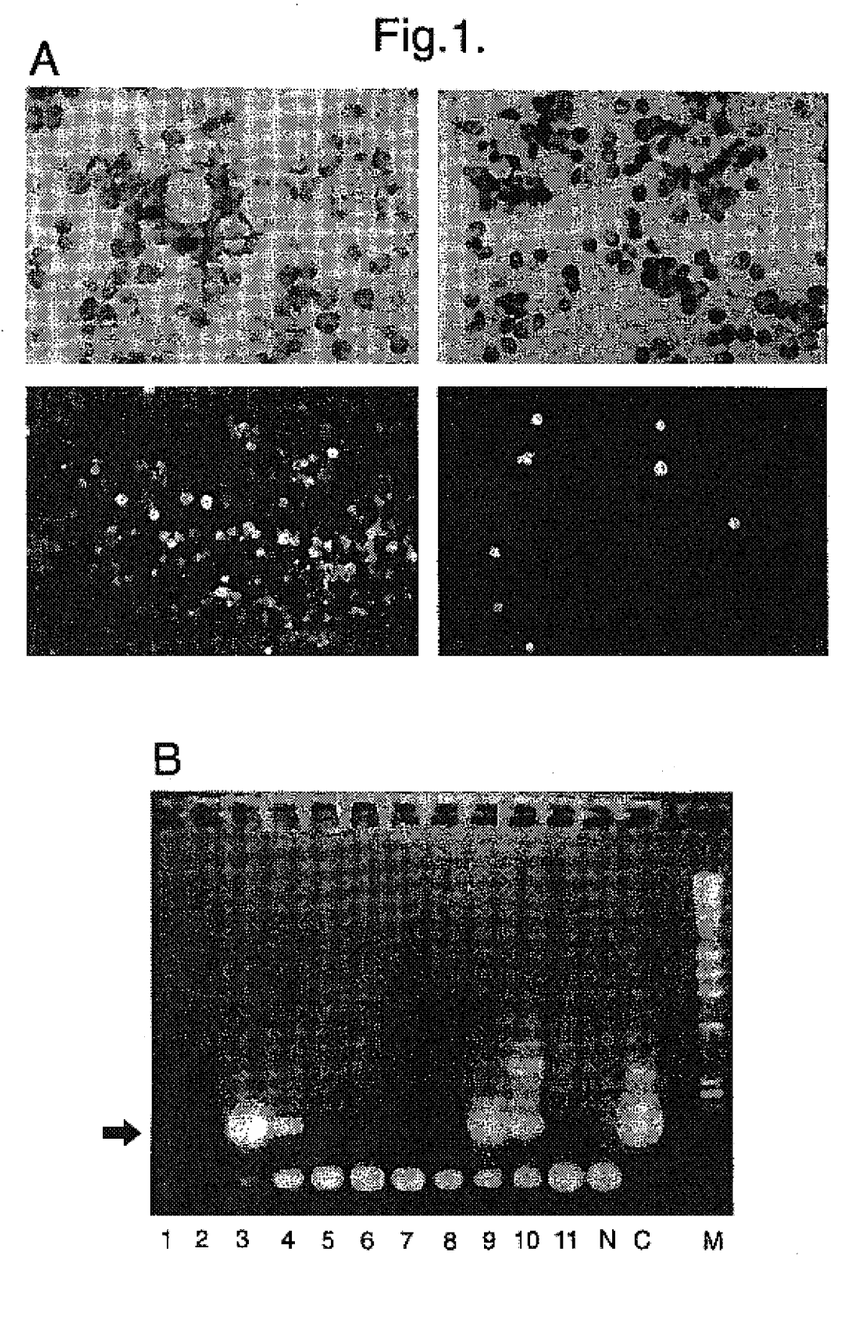
FIG. 1. A) top panels, bone marrow cells following 5 days incubation with 5-FU (right) or without 5-FU (left); bottom panels, staining of cells as above for SCF receptor at completion of 7 days selection in 5-FU (right) or without 5-FU (left). B) PCR analysis of colonies arising from retrovirally transduced, 5-FU selected, stem cells in semi-solid medium following 4 weeks long term culture. 1–9, colonies; N, negative control; C, positive control; M, size markers. The arrow indicates the retroviral PCR product.
Figure 2:
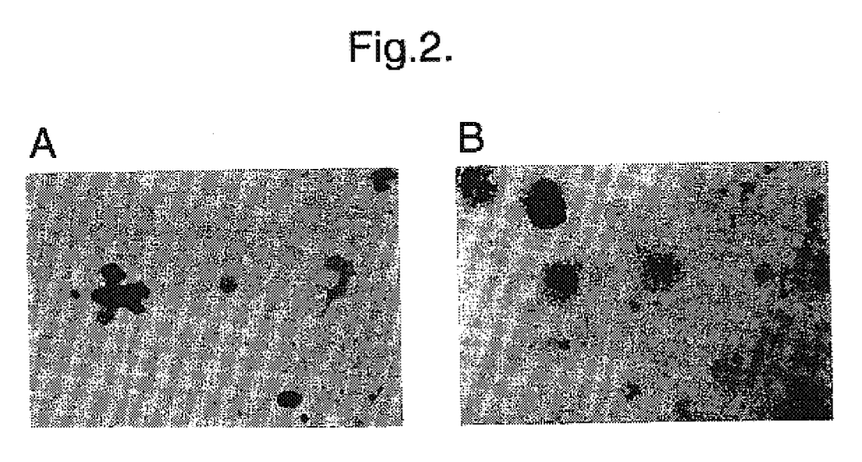

Bone marrow cells (10 mls; approx $5 \times 10^7$ cells) were aspirated from the iliac crest of normal volunteers under local anaesthesia. The cells were washed twice with sterile PBS, re-pelleted and layered onto the surface of a discontinuous ficoll gradient. Cells were separated by centrifugation for 20 mins at 2500 rpm. Mononuclear cells were removed from the interphase and washed with PBS. Cells were then incubated in Iscove's DMEM medium supplemented with 10% fetal calf serum, 5-fluorouracil (5-FU), stem cell factor (SCF) and IL-3, as described by Beradi et al (Science 267 1995) Following seven days in selection (see FIG. 1A), the surviving cells were co-cultured for 48 hrs in the presence of the SCF-producer line. Following co-cultivation, they were removed from the producers and used to establish long term cultures (LTC) on heterologous irradiated human stroma, in McCoy's medium modified for long term culture. After 4 weeks in LTC, cells were plated in semi-solid media containing cytokines (StemGEM™), to allow colonies to develop.

(c) Detection of Transduced Cells

Transduction was scored by PCR analysis of colonies (FIG. 1B). The PCR relied on a nested strategy using two upstream and one downstream primers. An initial round of 35 cycles of amplification using the most upstream primer and the downstream primers was performed. A small aliquot of this reaction was removed and re-amplified in a second reaction using the second upstream primer and the downstream primer. The most upstream primer is complementary in sequence to a region from the gag gene of the retroviral vector and the other two primers are complementary to different regions from the p47-phox cDNA sequence. The size of the initial product is 454 nucleotides and the nested product 180 nucleotides. This strategy ensures that the PCR product is specific for the retrovirally encoded p47-phox gene and not the endogenous gene. The products of the PCR amplification were visualised under ultra-violet light (300 nm) following separation by standard agarose gel electrophoresis on 2% gels containing ethidium bromide.

TABLE 1

PCR Colony Data (Ethidium Bromide Staining)

| Experiment | +Colonies/Total SCF | +Colonies/ Total Control | % + SCF | % + Control | Fold increase with SCF |
|---|---|---|---|---|---|
| 1 | 5/20 | — | 25 | — | — |
| 2 | 5/30 | 0/30 | 17 | 0 | >5 |
| 3* | 11/30 | 1/30 | 37 | 3 | 11 |
| 4 | 19/30 | 7/20 | 63 | 35 | 2 |
| 5 | 5/30 | — | 17 | — | — |
| 6 | 4/30 | 0/30 | 13 | 0 | >4 |

*Expt 2 re-evaluated using Southern Blot hybridisation.

The data set out in table 1 shows that in five separate experiments on marrow cell cultures indicated that is approximately 13% and 63% of colonies were positive for the presence of the retroviral genome, showing that the retroviral vector had succeeded in delivering the p47-phox gene to the PHSCs.

In addition, the data presented as experiment 2 was re-evaluated using a different, more sensitive, method (Southern blotting), demonstrating an 11-fold increase in the rate of transduction of the 5FU-selected PHSC following exposure to the retroviral producers that express stem cell factor on their surface. As no positive colonies were obtained from the controls in two experiments (Experiments 2 and 6), the increased rates of transduction can only be expressed as greater than 5 or 4 times better than the control respectively. These values can therefore be considered as the absolute minimum in terms of the benefit of using the SCF-expressing producers; the actual value may be considerably greater.

(iv) PCNA Staining

A nuclear antigen referred to as "proliferating cell nuclear antigen" (PCNA) a component of the DNA replication machinery can be used as a marker of cells in the process or capable of undergoing cell division. As such, staining cells with antibody to this antigen can give information on the cycling status of cells in a chosen population. Staining of PHSC selected by the 5FU technique with a monoclonal antibody to PCNA (PC10), revealed that the majority of the cells (~90%, FIG. 1a and Table 2) were unlabelled and were therefore quiescent, as expected. These cells were then cultured for 48 hours in the presence of the SCF-expressing producer line or the control parent cell line and stained with the PC10 antibody. Cells that had been exposed to the SCF producers showed a marked increase in the fraction of positively staining cells (~50% and table 2).

TABLE 2

|  | PCNA staining | | |
| --- | --- | --- | --- |
| Cells | +cells* | Total + cells | % + cells |
| 5FU cells | 8/73 | 3/42 | 11/115 | 9.5 |
| Post SCF | 9/17 | 9/18 | 18/35 | 51.4 |
| Post Control | 0/10 | — | 0/10 | 0 |

*Cells were counted from two different random views under microscopical examination. Insufficient control cells were obtained to enable two counts to be made.

EXAMPLE 4

Production of a Retrovirus Displaying Surface Bound Growth Factor as an N-terminal Extension of the Viral Envelope SU Protein (a) Construction of Chimeric Envelope Expression Plasmids Plasmids were created encoding chimeric envelopes in which stem cell factor (SCF) or Flt3 ligand (FL) is fused to the first codon of the SU envelope glycoprotein as a factor Xa cleavable or non-cleavable N-terminal extension of the 4070A (amphotropic) murine leukaemia virus (MLV).

Figure 8:
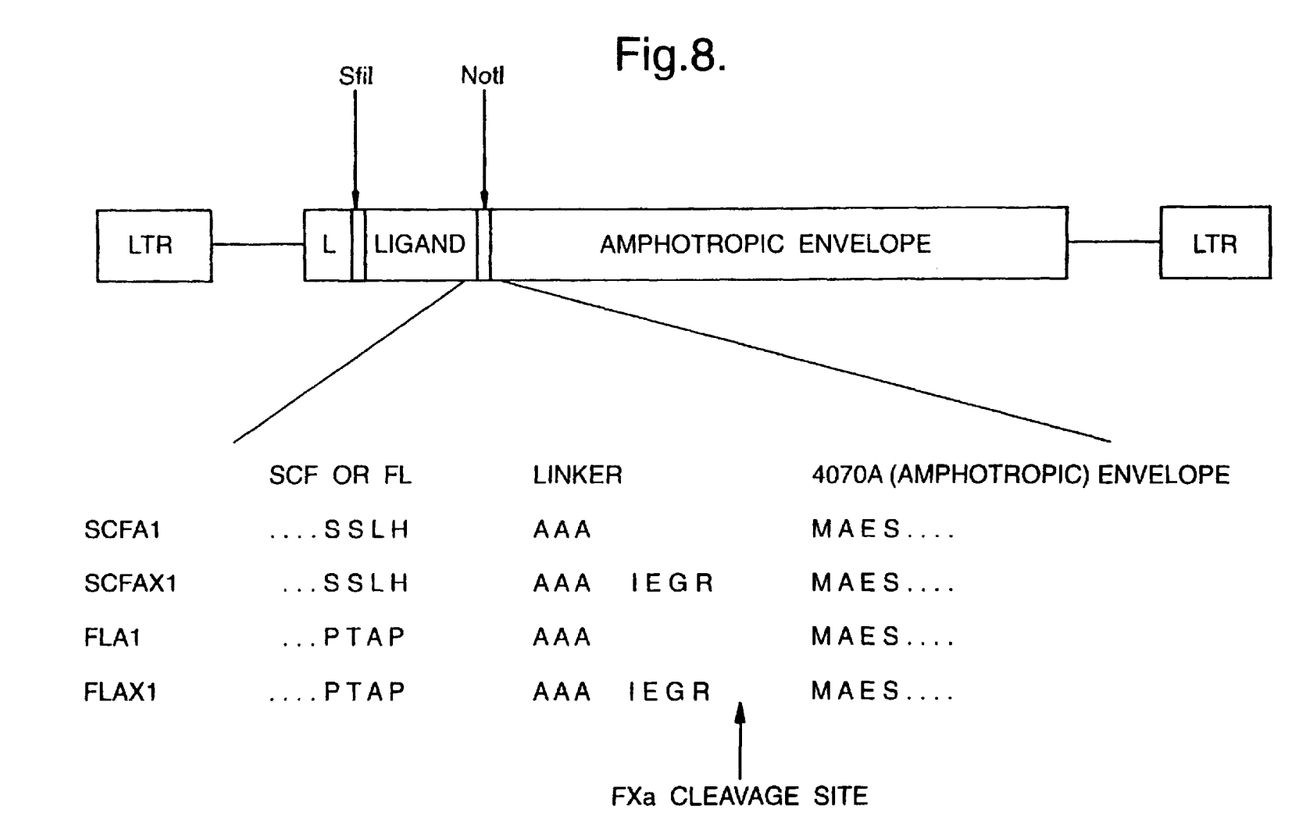
FIG. 8 shows a diagrammatic representation of the plasmid constructs (SCFA1, SCFAX1, FLA1, and FLAX1, SEQ ID NOs:1–4, respectively) used in example 4 in the production of retrovirus displaying surface bound growth factor as an N-terminal extension of the viral envelope SU protein.

SCF and FL cDNA was PCR amplified and tailed with Sfil and Not 1 restriction sites. The PCR products were cloned into existing chimeric envelope expression plasmids EA1 and EXA1 (10) after digestion with the restriction enzymes Sfil and Not 1. FIG. 8 shows a diagrammatic representation of the plasmid constructs. The sequences of all the constructs was confirmed by dideoxysequencing.

(b) Production of Viruses

The chimeric envelopes and control amphotropic (4070A) envelopes were expressed in TelCeB.6 complementing cells, which express MLV gag-pol core particles and a nlsLacZ retroviral vector. Envelope expression plasmids were transfected by calcium phosphate precipitation into the TelCeB.6 cells. Transfected cells were selected with phleomycin and blasticidin in DMEM supplemented with 10% foetal calf serum (FCS) and grown to confluency. Viral supernatants were harvested from stably transfected cells after overnight incubation in either serum free DMEM or DMEM containing 10% FCS and filtered with a 0.45 µm filter for use in infection or binding experiments. For immunoblotting, viral supernatants were filtered (0.45 µm) and then pelleted by ultracentrifugation at 30,000 rpm in a SW40 rotor for one hour at 4° C. The pelleted viral particles were re-suspended in 100 µl of phosphate buffered saline and stored at −20° C.

(c) Target Cells

The murine cell line NIH 3T3 was grown in DMEM supplemented with 10% FCS. The human SCF receptor (Kit) expressing cell line HMC-1 was grown in Iscove's modified Dulbecco's eagle medium (IMDM) supplemented with 10% FCS and monothioglycerol. The human kit negative cell line K422 was grown in RPMI supplemented with 10 FCS.

(d) Immunoblots

Ten µl of the pelleted viral particles were separated on a 10% polyacrylamide gel under reducing conditions and subsequently transferred to nitrocellulose. The viral SU proteins were detected using a primary goat anti-envelope antibody. Blots were developed using a secondary anti-goat antibody conjugated to horseradish peroxidase and an enhanced chemiluminescence kit.

(e) Infections

Target cells were plated into six-well plates at approximately $10^5$ cells per well and incubated overnight at 37° C. (adherent cells) or plated into six well plates at approximately $10^6$ cells per well one hour before infection (suspension cells). Filtered viral supernatant in serum free medium was added to the target cells and incubated for 4 hours in the presence of 8 µg/ml polybrene.

The retroviral supernatant was then removed from the target cells, the medium was replaced with the usual medium and the cells were placed at 37° C. for a further 48–72 hours. X-gal staining for detection of β-galactosidase activity was carried out as previously described (11). Viral titre was calculated by counting blue stained colonies microscopically and expressed as enzyme forming units per ml (adherent cells) or percentage blue stained cells (suspension cells).

(f) Immunoblotting of Pelleted Virus

Figure 9:
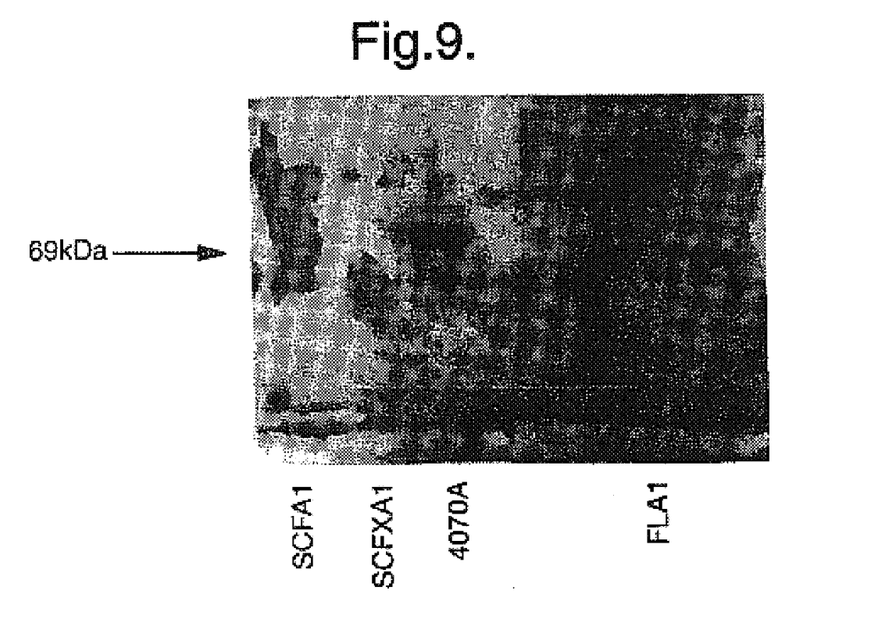
FIG. 9 is a Western blot showing the chimeric envelope proteins of SCF and FL displaying viruses.
Figure 10:
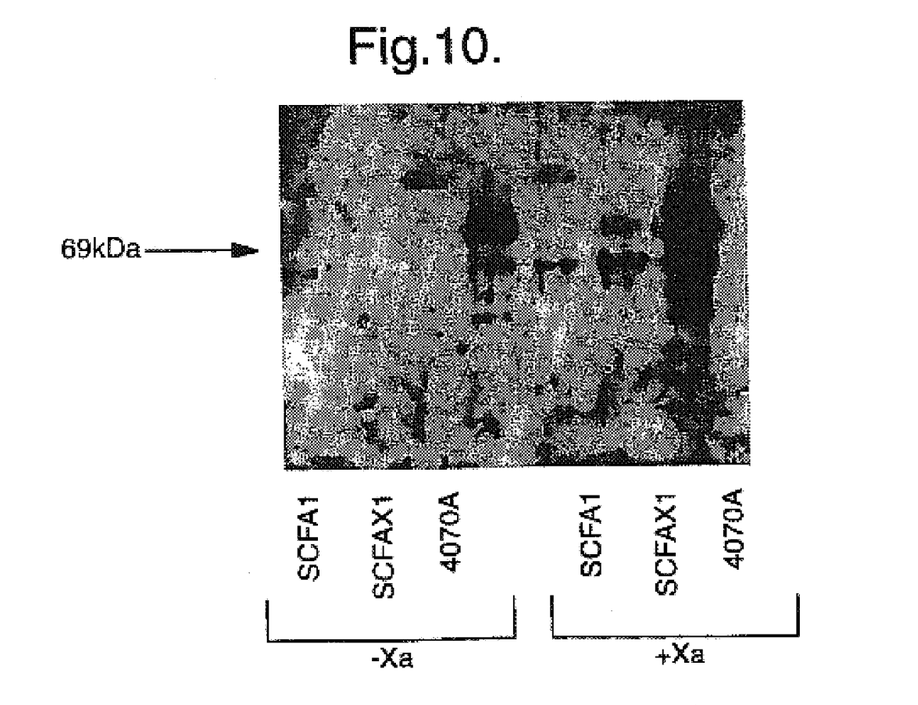
FIG. 10 is a Western blot showing specific cleavage at the factor $X_a$ cleavage site of SCFAX1 that upon treatment of the viral pellets with $FX_a$ protease.

The viral pellets of both SCF and FL displaying viruses were analysed by immunoblotting and a representative blot is shown in FIG. 9. The presence of chimeric viral envelope with a distinct mobility from that of the wild type virus is demonstrated. FIG. 10 shows that upon treatment of the viral pellets with 4 µg/ml $FX_a$ protease, the $FX_a$ cleavage signal in the interdomain linker of the expressed envelope SCFXA1 is correctly recognised and cleaved to yield a SU cleavage product with identical mobility to the unmodified 4070A envelope SU.

(g) Host Range Properties of Vectors Incorporating the Chimeric Envelopes

Viral supernatant harvested from cells transfected with the various constructs was used to infect mouse fibroblasts. Gene delivery to the 3T3 cells was demonstrated for the amphotropic chimeras and was unaffected by protease cleavage. Thus viral infectivity mediated by the underlying envelope was not blocked by display of these dimeric ligands.

Figure 11:
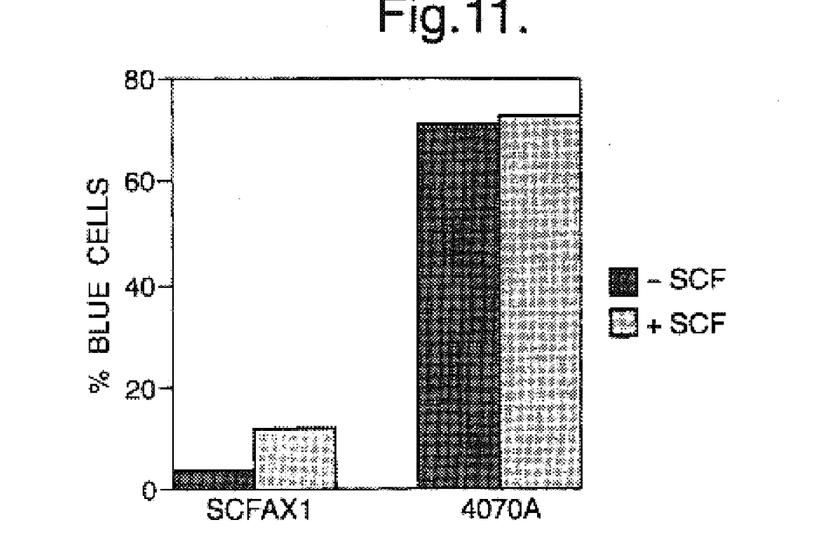
FIG. 11 shows the effect of SCF competition on tropism of retroviral vectors displaying SCF.
Figure 12:
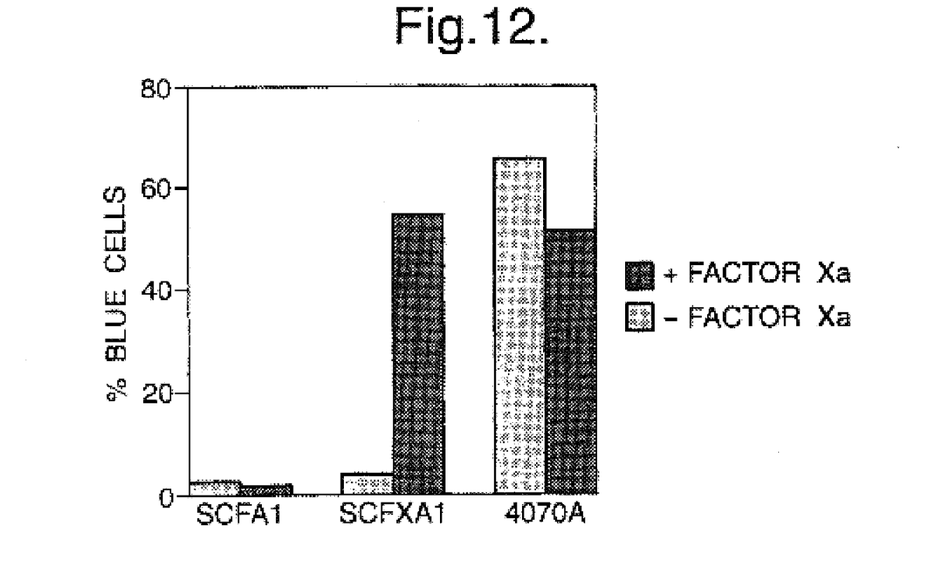
FIG. 12 shows tropism of retroviral vectors displaying cleavable and non-cleavable SCF for Kit positive cells.
Figure 13:
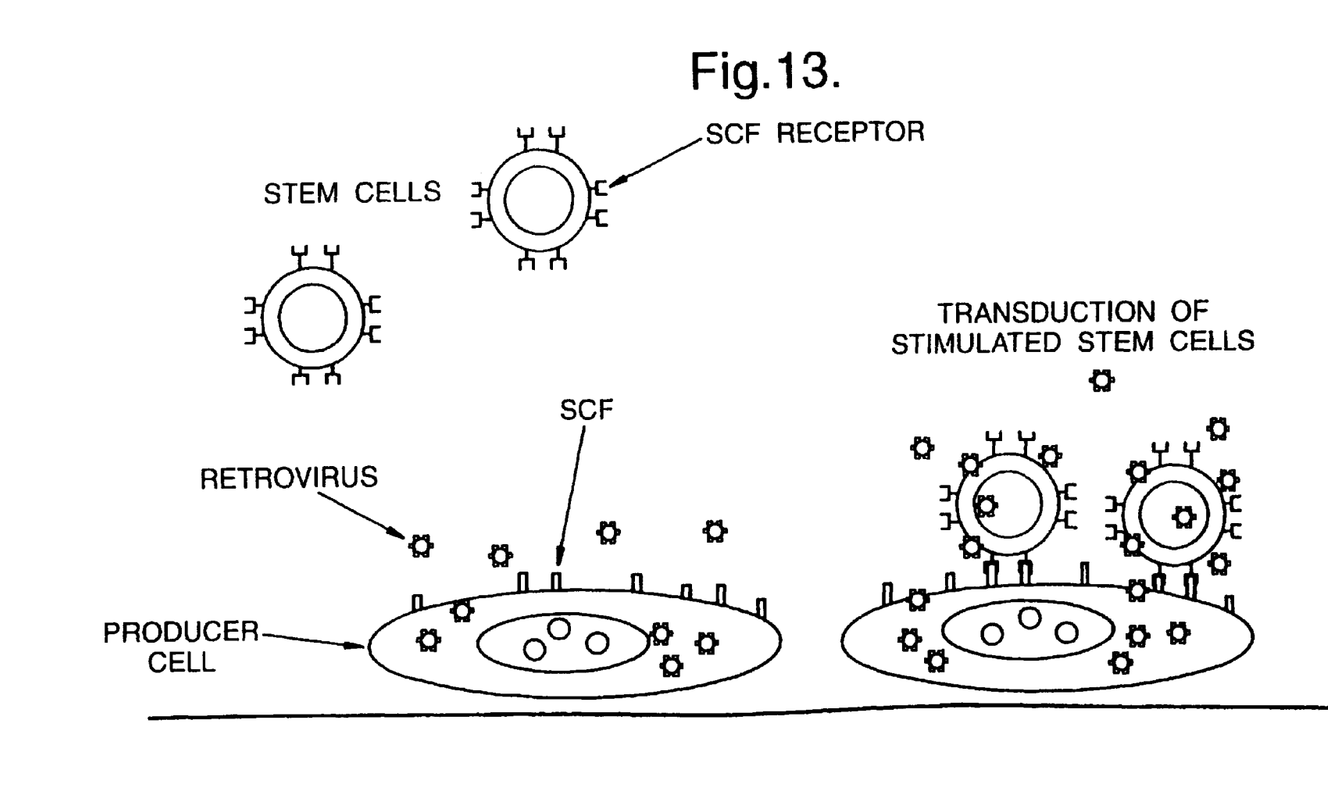
FIG. 13 shows a schematic representation of the transduction of stem cells using retroviral packaging cell lines expressing membrane bound SCF.

The infectivity of viruses incorporating the SCFA1 and SCFXA1 chimeric envelopes was tested on HMC-1 cells—a human Kit expressing cell line. Both vectors were capable of binding to Kit positive cells but gave very low titres compared to the wild type vector. When soluble SCF was added as competitor to prevent the vectors from binding to Kit, the infectivity was increased, suggesting that the reduced ability of these vectors to bind to Kit positive cells was a consequence of targeted binding to SCF receptors (FIG. 11). These vectors were then treated with factor $X_a$ protease prior to infection. Pre-incubation with FXa had no effect on the titre of the SCFA1 vector but restored the titre of SCFXA1 to that of the wild-type amphotropic vector (FIG. 12). This effect of $FX_a$ cleavage did not occur on the Kit negative cell line K422. This data provides evidence that retroviral vectors displaying SCF are capable of selectively binding to human cells expressing Kit but that infection of Kit positive cells cannot take place until the engineered binding domain has been cleaved. In this respect, this ligand-receptor systems resembles the EGF system developed in our laboratory (11) and is potentially amenable to the two-step targeting strategies developed for EGF.

Discussion

The above results show that good levels of transduction of PHSC can be achieved using engineered retroviral packaging cells expressing human SCF on their cell surface. Thus, the results above indicate that the cells should be capable of simultaneously delivering both a growth signal and a retroviral vector to the target PHSC. This simultaneous delivery of vector and growth signal should also have the advantage of increasing the effective retroviral titre, owing to the intimate association of producer and target cells.

SCF has been shown to have both soluble and membrane-bound forms. Evidence acquired from the study of mice carrying a small intragenic deletion in the gene encoding the SCF receptor has indicated that the membrane-bound form of the cytokine is essential for normal haematopoiesis. Despite being able to synthesise a soluble SCF retaining full biological activity, these mice are as badly affected as their counterparts who carry a complete deletion of the gene. While not wishing to be bound by any particular theory, we believe that the in vivo biological activities of the soluble and membrane-associated forms of the growth factor are distinct, and that normal haematopoiesis has an absolute requirement for the membrane-bound form of SCF that cannot be substituted by the soluble form. It may also be that the expression of bound SCF on the cell surface changes/reduces the extent to which other growth factors are expressed, and that this has a beneficial effect on transduction levels of the PHSC.

Improved transduction rates using the method may be achieved using the synergistic action of additional cytokines. In this regard, SCF is particularly noted for its property of interacting in this way with other growth factors, which has led to the suggestion that on its own it may not be a mitogen but acts as an anti-apoptotic factor. To assess this, similar experiments to those described above can be performed using additional cytokines added to the media in conjunction with our modified producers. Ideally, we would hope to find conditions favouring self-renewal at the expense of differentiation. This would have the highly desirable consequence of enabling us to expand PHSC numbers in culture. One factor thought possibly to act in this way is MIP1-α1. There is also evidence that stem cell quiescence may be negatively influenced by TGF-β, antagonists of this molecule may therefore be beneficial in stimulating cells into cycle. Of the positively acting cytokines, LIF, the factor that blocks differentiation of mouse embryonal stem cells and IL-11, a recently identified member of the same family of cytokines, are candidates for acting on stem cells, as is flt3 ligand, a molecule with a similar spectrum of activities to SCF.

As regards embodiments of the invention using growth factors displayed on the surface of retroviruses, the results presented above demonstrate that the dimeric ligands SCF and FL can successfully be displayed on retroviruses and that these ligands retain the capability of binding to their receptors. We have demonstrated that, although infection cannot be mediated through the displayed ligand, if a protease cleavable linker is used to fuse the displayed ligand to the viral envelope, targeted infection can result. The modified viruses described here retain their capacity to infect cells through the Ram1 receptor but other results from our laboratory indicate that it is possible to construct a cleavable linker which is capable of blocking infection through the natural viral receptor. In should therefore be possible to target retroviral gene transfer specifically to PHSC.

The above method describes a protocol which is potentially applicable to any clinical procedure requiring the transfer of genetic information to pluripotent haematopoeitic stem cells (PHSC). As discussed above, this method is applicable for gene therapy of inherited haematopoeitic disorders, such as the immunodeficiencies, but it could also be applicable to conditions such as haemophilia, or other conditions requiring the synthesis of a pharmacologically active compound normally present in the serum. There are also potential applications in the field of cancer therapy, primarily as a way of protecting cells from cytotoxic agents or radioprotecting them, thus giving them a survival advantage over non-treated bone marrow cells.

References

The references mentioned in this application are all herein incorporated by reference.

1. Markowitz, D., S. Goff, and A. Bank. 1988. Construction and use of a safe and efficient amphotropic packaging cell line. *Virology* 167:400.
2. Thrasher, A., M. Chetty, C. Casimir, and A. W. Segal. 1992. Restoration of Superoxide Generation to a Chronic Granulomatous Disease-Derived B-Cell Line by Retrovirus Mediated Gene Transfer. *Blood* 80:1125.
3. Morgenstern, J. P. and H. Land. 1990. Advanced mammalian gene transfer: high titre retroviral vectors with multiple drug selection markers and a complementary helper-free packaging cell line. *Nucleic Acids Res.* 18:3587.
4. Anderson, D. M., D. E. Williams, R. Tushinski, S. Gimpel, J. Eisenman, L. A. Cannizzaro, M. Aaronson, C. M. Croce, K. Huebner, and D. Cosman. 1991. Alternate splicing of mRNAs encoding human mast cell growth factor and localisation of the gene to chromosome 12q22–12q24. *Cell Growth Differ* 2:373.
5. Beradi, A. C., A. Wang, J. D. Levine, P. Lopez, and D. T. Scadden. 1995. Functional isolation and characterization of human hematopoietic stem cells. *Science* 267:104.
6. Mullis, K., F. Faloona, S. Scharf, R. Saiki, G. Horn, and H. Erlich. 1986. Specific enzymatic amplification of DNA in vitro: the polymerase chain reaction. *Cold Spring Harb Symp Quant Biol* 51:263.
7. Russell, S. J., R. E. Hawkins, and G. Winter, 1993. Retroviral vectors displaying functional antibody fragments.
8. Valesia-Wittman, S., A. Drynda, G. Delange, M. Aumailley, J. M. Heard, O. Danos, G. Verdier, and F. L. Cosset. 1994. Modifications in the binding domain of avian retrovirus envelope protein to redirect the host range of retroviral vectors. *J. Virol.*, 68:4609.
9. Kasahara, N., A. M. Dozy and Y. N. Kan. 1994. Tissue-specific targeting of retroviral vectors through ligand-receptor interactions. *Science*, 266:1373.
10. Nilson B H K, Morling F J, Cosset F-L, Russell S. J. Targeting of retroviral vectors through protease-substrate interactions. Gene Therapy 1996, 3:280–286.
11. Takeuchi Y et al. Type C retrovirus inactivation by human complement is determined by both the viral genome and the producer cell. J Virol 1994, 68: 8001–8007.
12. Bagnis, C., Gravis, G., Imbert, A. M., Herrera, D., Allario, T., Galindo, R., Lopez, M., Pavon, C., Sempere, C., and Mannoni, P. (1994). Retroviral transfer of the nlsLacZ gene into human CD34+ cell populations and into TF-1 cells: future prospects in gene therapy. Hum. Gene Ther., 5, 1325–1333.
13. Broxmeyer, H. E., Lu, L., Cooper, S., Ruggieri, L., Li, Z. H., and Lyman, S. D., (1995). Flt3 ligand stimulates/costimulates the growth of myeloid stem/progenitor cells. Exp. Hematol., 23, 1121–1129.
14. Einerhand, M. P., Bakx, T. K., and Valerio, D., (1991). IL-6 production by retrovirus packaging cells and cultured bone marrow cells. Hum. Gene Ther., 2, 301–306.
15. Krause, D. S., Fackler, M. J., Civin, C. I., and May, W. S., (1996). CD34: structure biology and clinical utility, Blood, 87, 1–13.
16. Leitner, A., Strobl, H., Fischmeister, G., Kurz, M., Romanakis, K., Haas, O. A., Printz, D., Buchinger, P., Bauer, S., Gadner, H., and Fritsch, G. (1996). Lack of DNA synthesis among CD34+ cells in cord blood and in cytokine mobilized blood. Br. Haematol 192, 255–262.

What is claimed is:

1. A method of transforming a quiescent cell with a nucleic acid encoding a polypeptide, the method comprising:
    exposing said quiescent cell in vitro to a retroviral packaging cell, said retroviral packaging cell comprising a retroviral vector and an exogenous nucleic acid encoding a growth factor, wherein said growth factor is displayed on the surface of said retroviral packaging cell, wherein said retroviral vector comprises said nucleic acid encoding said polypeptide, and
    wherein said growth factor displayed on the surface of said retroviral packaging cell induces said quiescent cell to divide, so that the nucleic acid encoding said polypeptide can incorporate into the genome of said quiescent cell.

2. The method of claim 1 wherein said quiescent cell is a hematopoietic stem cell.

SEQUENCE LISTING

<160> NUMBER OF SEQ ID NOS: 4

<210> SEQ ID NO 1
<211> LENGTH: 11
<212> TYPE: PRT
<213> ORGANISM: Artificial Sequence
<220> FEATURE:
<223> OTHER INFORMATION: plasmid construct

<400> SEQUENCE: 1

Ser Ser Leu His Ala Ala Ala Met Ala Glu Ser
1               5                   10

<210> SEQ ID NO 2
<211> LENGTH: 15
<212> TYPE: PRT
<213> ORGANISM: Artificial Sequence
<220> FEATURE:
<223> OTHER INFORMATION: plasmid construct

<400> SEQUENCE: 2

Ser Ser Leu His Ala Ala Ala Ile Glu Gly Arg Met Ala Glu Ser
1               5                   10                  15

<210> SEQ ID NO 3
<211> LENGTH: 11
<212> TYPE: PRT
<213> ORGANISM: Artificial Sequence
<220> FEATURE:
<223> OTHER INFORMATION: plasmid construct

<400> SEQUENCE: 3

Pro Thr Ala Pro Ala Ala Ala Met Ala Glu Ser
1               5                   10

<210> SEQ ID NO 4
<211> LENGTH: 15
<212> TYPE: PRT
<213> ORGANISM: Artificial Sequence
<220> FEATURE:
<223> OTHER INFORMATION: plasmid construct

<400> SEQUENCE: 4

Pro Thr Ala Pro Ala Ala Ala Ile Glu Gly Arg Met Ala Glu Ser
1               5                   10                  15

3. The method of claim 1 wherein the growth factor is stem cell factor (SCF) or FLT3 ligand.

4. The method of claim 1 wherein said retroviral packaging cell displaying said growth factor on its surface displays multiple growth factors.

5. The method of claim 1 wherein said growth factor is expressed as an N-terminal fusion protein with a retroviral envelope protein.

6. The method of claim 1 wherein said growth factor is expressed as a fusion protein with a viral envelope protein and is fused to the envelope protein via a cleavable linker.

7. The method of claim 5 wherein said retroviral envelope protein is viral envelope SU protein.

8. The method of claim 1 wherein said retroviral packaging cell displaying said growth factor on its surface further expresses nucleic acid encoding a receptor to target the retroviral packaging cell to the bone marrow and/or an immunosuppressive factor so that the receptor and/or immunosuppressive factor are displayed on the cell surface of said retroviral packaging cell.

* * * * *